United States Patent [19]

Matsui et al.

[11] Patent Number: 4,527,070
[45] Date of Patent: Jul. 2, 1985

[54] METHOD AND APPARATUS FOR INSPECTING A PATTERN

[75] Inventors: Shougo Matsui, Sagamihara; Yoshimitu Mashima, Kawasaki; Kenichi Kobayashi, Tokyo, all of Japan

[73] Assignee: Fujitsu Limited, Kawasaki, Japan

[21] Appl. No.: 409,983

[22] Filed: Aug. 20, 1982

[30] Foreign Application Priority Data

Aug. 20, 1981 [JP] Japan .................................. 56-131276

[51] Int. Cl.³ .............................................. G01N 21/86
[52] U.S. Cl. ..................................... 250/560; 356/376
[58] Field of Search ........................ 364/468, 488–491; 250/556, 560; 358/101, 106; 356/400, 376

[56] References Cited

U.S. PATENT DOCUMENTS

| 4,318,081 | 3/1982 | Yoshida | 364/468 |
| 4,390,955 | 6/1983 | Arimura | 358/101 |
| 4,414,566 | 11/1983 | Peyton et al. | 358/101 |
| 4,445,137 | 4/1984 | Panofsky | 358/101 |

Primary Examiner—David C. Nelms
Assistant Examiner—J. Jon Brophy
Attorney, Agent, or Firm—Staas & Halsey

[57] ABSTRACT

In a method for inspecting a pattern produced by using pattern data of a predetermined reference pattern, comparison is carried out between the pattern reproduced from the scanning signal of the pattern and the pattern produced from the signal of a modified form of the predetermined reference pattern.

12 Claims, 8 Drawing Figures

METHOD AND APPARATUS FOR INSPECTING A PATTERN

BACKGROUND OF THE INVENTION

The present invention relates to a method and an apparatus for inspecting a pattern. The method of the present invention is used, for example, to inspect the pattern formed on a reticle used for producing master masks for producing semiconductor devices.

Photomasks used for producing semiconductor devices are produced by producing a pattern on a reticle approximately 10 times the size of the photomask, reducing the reticle to obtain a master mask, and copying the master mask. The reticle pattern is usually inspected using a microscope. However, such an inspection method requires a considerable number of steps. Further, the accuracy of the inspection is not satisfactory.

It is possible to inspect the reticle pattern using the apparatus illustrated in FIG. 1, which will be introduced later in the brief description of the drawings. The apparatus of FIG. 1 comprises a glass plate 1 having a reticle pattern 11, a light source 2 emitting a light beam L1, an image sensor 3 comprising, for example, a charge coupled device (CCD) receiving light beam L2, a pattern signal conversion circuit 41 for receiving the signal from the image sensor 3, an actual pattern display device 42 comprising, for example, a TV monitor for receiving the signal from the pattern signal conversion circuit 41, a memory device 51 comprising, for example, a magnetic tape, a pattern signal conversion circuit 52 for receiving the signal from the memory device 51, a reference pattern display device 54 comprising, for example, a TV monitor for receiving the signal from the pattern signal conversion circuit 52, a comparator circuit 61 for receiving the signals from the pattern signal conversion circuits 41 and 52, and a memory device 62 comprising, for example, a magnetic tape for receiving the signal from the comparator circuit 61.

Figure 1:
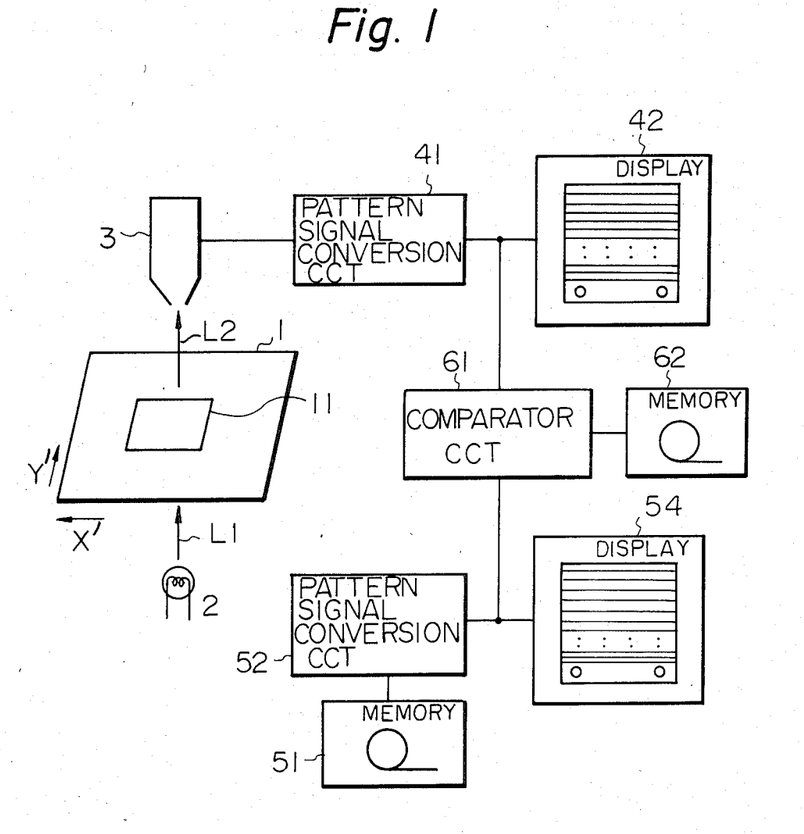
FIG. 1 is an apparatus for inspecting a pattern according to a background art of the method and apparatus of the present invention.

In the device of FIG. 1, the actual reticle pattern 11 on the plate 1 is scanned with the light beam L1 emitted from the light source 2 by moving the glass plate 1 in the X' direction from right to left, in the reverse-X' direction from left to right, in the Y' direction by a predetermined amount, in the X' direction from right to left, and then in the reverse-X' direction from left to right, and so on.

The pattern signal produced from the image sensor 3 is converted in the pattern signal conversion circuit 41 to output a signal to the actual pattern display device 42 and the comparator circuit 61. The reference pattern signal is read out from magnetic tape 51 and supplied to the pattern signal conversion circuit 52 which outputs a signal to the reference pattern display device 54 and the comparator circuit 61. The actual pattern and the reference pattern can therefore be visually compared and checked on the display devices 42 and 54.

Figure 4:
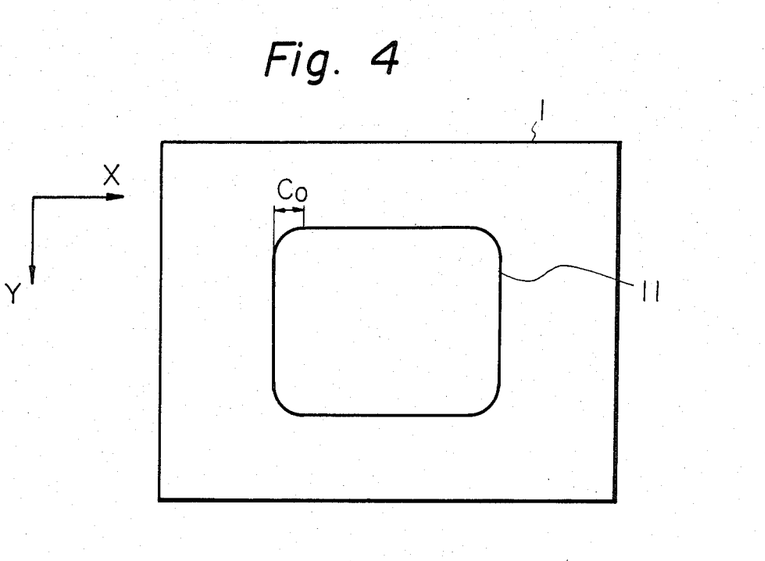
FIG. 4 is an example of the pattern to be inspected.

In the operation of the device of FIG. 1, there exists the problem of missing the corners of the actual reticle pattern 11. That is, the etching process using the photo resist layer as a mask and applied to the metal layer unavoidably causes loss of the corners of the actual reticle pattern. Hence, an actual reticle pattern with missing corner portions is obtained, as illustrated in FIG. 4. The actual reticle pattern 11 of FIG. 4 has round corners. The length $C_0$ of one of the round corners in the X direction is, for example, less than approximately 1.2 microns. While actual patterns with missing corners of more than 1.2 micron $C_0$ should be excluded as defective, actual patterns with the missing corners of less than 1.2 micron $C_0$ should be regarded as permissible even if they do not coincide exactly with the reference pattern.

However, since the reference pattern read out from the magnetic tape 51 is the precisely designed pattern, the reference pattern has no such round corners as in the actual pattern. Therefore, in the device of FIG. 1, it is desired that the result of the comparison between the actual pattern and the reference pattern indicate the actual pattern to be defective only when the length $C_0$ of the round corner of the actual pattern exceeds a predetermined threshold length, such as 1.2 micron.

SUMMARY OF THE INVENTION

It is the principal object of the present invention to solve the above-described problem in the device of FIG. 1, to provide an improved method for inspecting patterns by comparing the actual patterns and a reference pattern, to avoid unnecessary detection of allowable defective patterns, to carry out the detection only with respect to substantially defective patterns, and, accordingly, to reduce the cost of the production of patterns, such as reticle patterns.

According to the fundamental aspect of the present invention there is provided a method for inspecting a pattern which is produced by using pattern data of a predetermined reference pattern, comprising the steps of scanning the pattern to be inspected to produce a scanning signal of the pattern, reading out the pattern data of the predetermined reference pattern stored in a memory device, processing the read out pattern data of the predetermined reference pattern to provide a modified signal of the predetermined reference pattern, the modified signal corresponding to a permissible pattern which is formed by deleting corners from the reference pattern, and comparing the scanning signal of the pattern and the modified signal of the predetermined reference pattern.

DESCRIPTION OF THE PREFERRED EMBODIMENT

Figure 2:
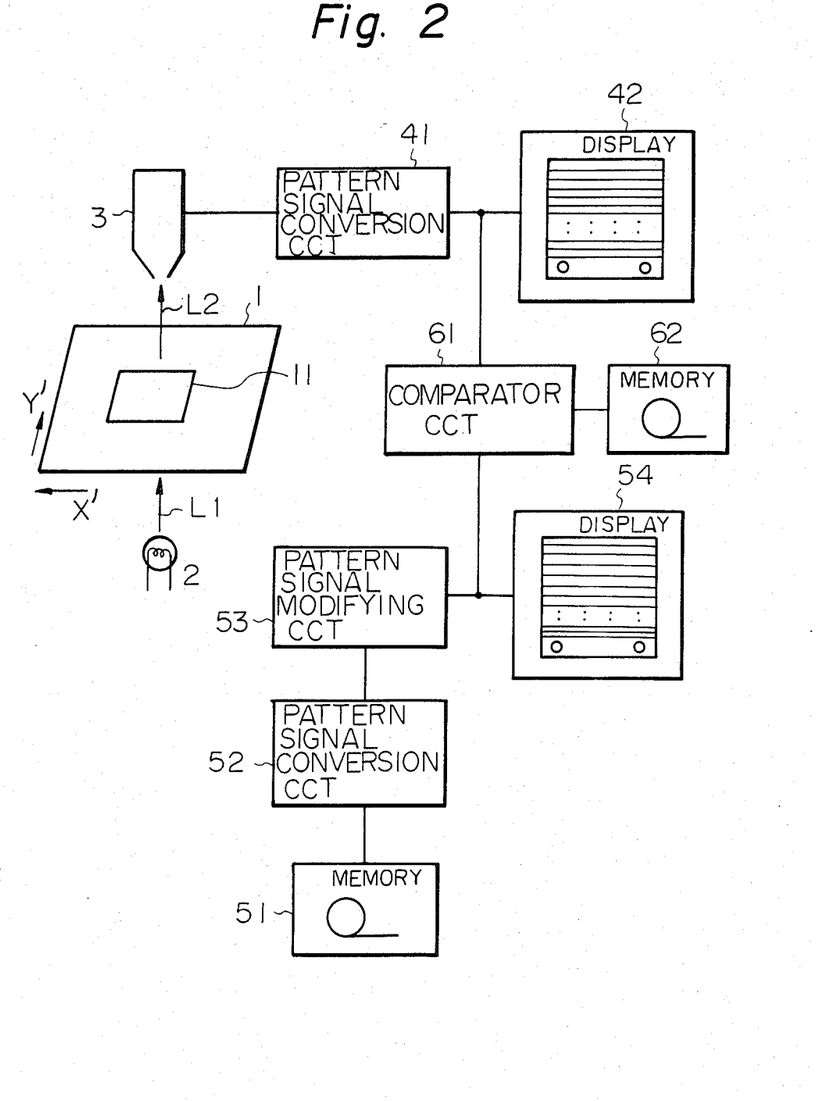
FIG. 2 is an apparatus for inspecting a pattern according to an embodiment of the present invention.

An apparatus for inspecting a pattern in accordance with an embodiment of the present invention is illustrated in FIG. 2. In this embodiment, the pattern 11 is on a reticle 1 which is used for producing a photomask for producing semiconductor devices.

The apparatus of FIG. 2 comprises a glass plate 1 having a reticle pattern 11, a light source 2 emitting a light beam L1, an image sensor 3 comprising, for example, a charge coupled device (CCD) for receiving a light beam L2, a pattern signal conversion circuit 41 for receiving the signal from the image sensor 3, an actual pattern display device 42 comprising, for example, a TV monitor for receiving the signal from the pattern signal conversion circuit 41, a memory device 51 comprising, for example, a magnetic tape, a pattern signal conversion circuit 52 for receiving the signal from the memory device 51, a pattern signal modifying circuit 53 for receiving the signal from the pattern signal conversion circuit 52, and a reference pattern display device 54 comprising, for example, a TV monitor for receiving the signal from the pattern signal modifying circuit 53.

The apparatus of FIG. 2 also comprises a comparator circuit 61 for receiving the signals from the pattern signal conversion circuit 41 and the pattern signal modifying circuit 53, and a memory device 62 comprising, for example, a magnetic tape for receiving the signal from the comparator circuit 61.

The pattern signal modifying circuit 53 carries out a modification of the reference pattern signal read out from the memory device 51 to produce a modified reference pattern with missing corners, that is, a modified reference pattern which is formed by deleting corners from the reference pattern.

Figure 3:
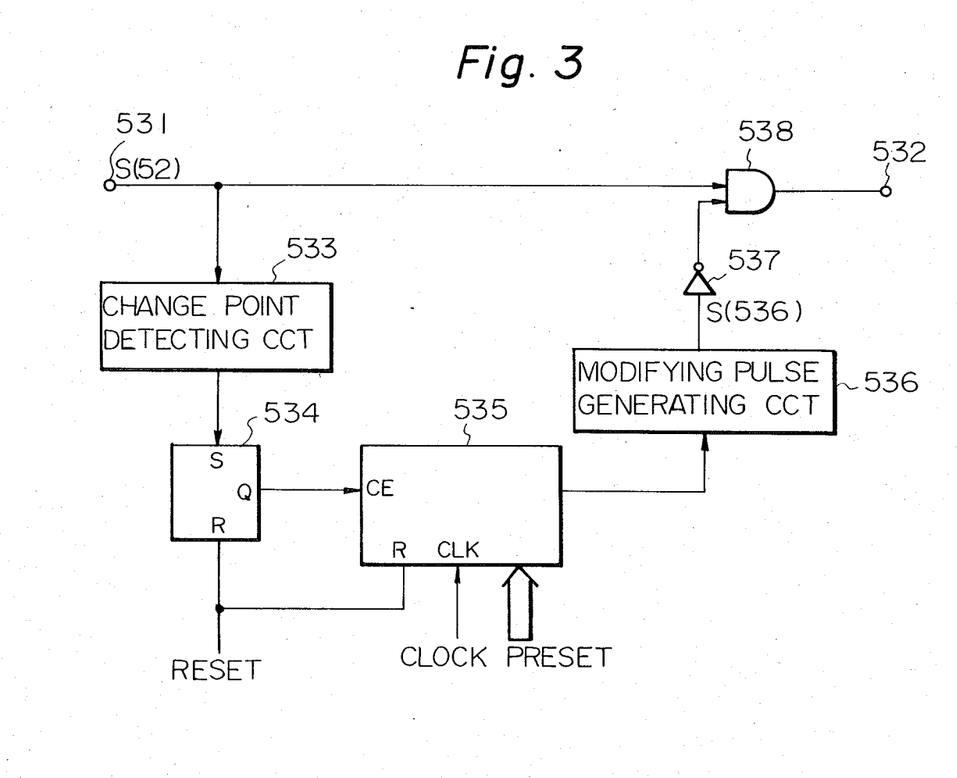
FIG. 3 is an example of the structure of the pattern signal modifying circuit 53 of FIG. 2.
Figure 6:
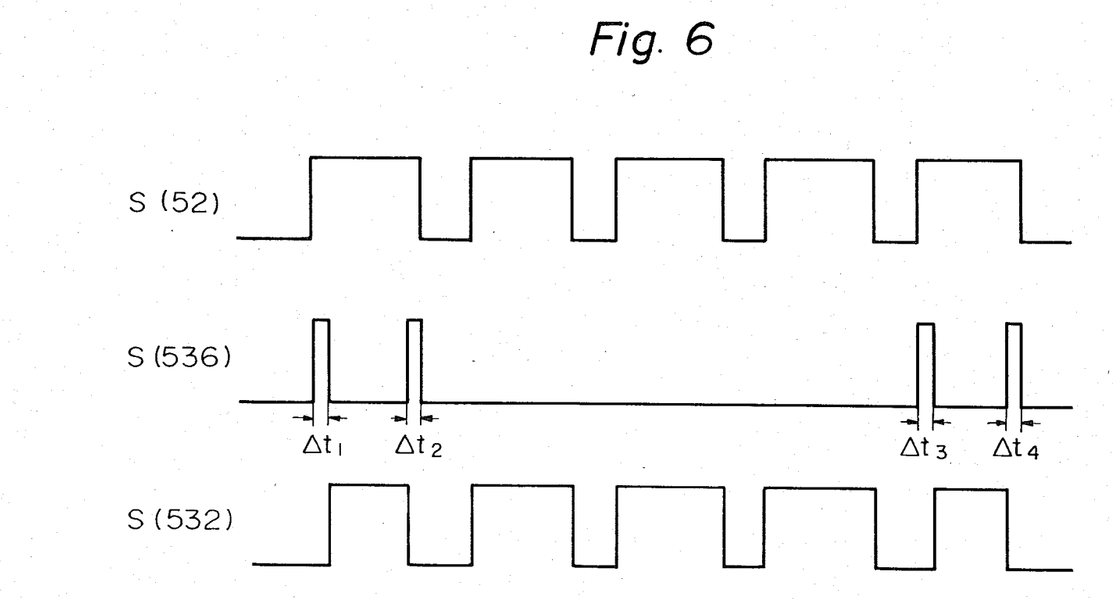
FIG. 6 is a waveform diagram of portions of the circuit of FIG. 3.

An example of the structure of the pattern signal modifying circuit 53 is illustrated in FIG. 3. The waveforms in the portions of the pattern signal modifying circuit 53 are illustrated in FIG. 6. The pattern signal modification circuit 53 comprises an input line 531, an output line 532, a change point detecting circuit 533, a set-reset circuit 534, a counter circuit 535, a modifying pulse generating circuit 536, an inverter 537, and an AND gate 538.

The pattern 11 on the glass plate 1 is scanned by the light beam L1 emitted from the light source 2 beneath the glass plate 1. The light beam L2 transmitted through the glass plate 1 is received by the image sensor 3 where the received light beam signal is transduced into an electrical signal. The output signal of the image sensor 3 is supplied to the pattern signal conversion circuit 41. The output signal of the pattern signal conversion circuit 41 is supplied to the actual pattern display device 42 and one input of the comparator circuit 61.

The modified reference pattern signal is produced by using the memory device 51, pattern signal conversion circuit 52, and pattern signal modifying circuit 53. The process of the production of the modified reference pattern signal will be described with reference to FIG. 5 which illustrates the scanning lines SC1 through SC5 on the reference pattern 11 (REF), and FIG. 6 which illustrates the waveform of the scanning signal.

The reference pattern signal S(52) is supplied to input terminal 531 of a change point detecting circuit 533. The change point detecting circuit 533 detects the point at which the indication of signal changes from white (light-transmitting) to black (light-interrupting), i.e., the point representing the edge of the pattern. The output signal of the change point detecting circuit 533 is supplied to the set-reset circuit 534. The Q output of the set-reset circuit 534 is supplied to an input terminal (CE) of the counter 535. In accordance with the output signal of the counter 535, the modifying pulse generating circuit 536 produces the modifying pulse signal S(536) illustrated in FIG. 6.

The width $\Delta t$, of the pulse S(536) is determined by the counter 535 which is controlled by the preset input signal PRESET.

Figure 5:
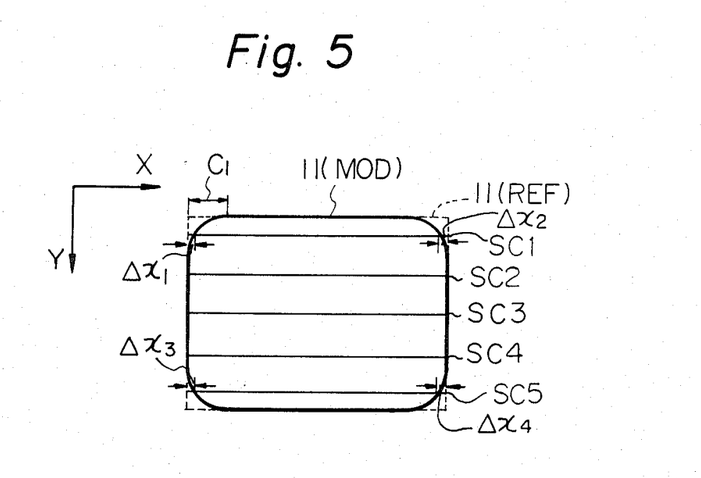
FIG. 5 is an example of the modified reference pattern.

The reference pattern 11 (REF) and the modified reference pattern 11 (MOD) are illustrated in FIG. 5. The reference pattern 11 (REF) has a precise rectangular shape. The modified reference pattern 11 (MOD), which is drawn in a solid line, has round corners. The length $C_1$ of the round corner corresponds to the length $C_0$ of the round corner of the actual pattern illustrated in FIG. 4.

Comparing FIG. 5 and FIG. 6, it will be understood that the width $\Delta t_1$ corresponds to the length $\Delta x_1$ along the scanning line SC1.

The output signal S(536) of the modifying pulse generating circuit 536 is supplied to the inverter 537. The output signal of the inverter 537 is supplied to one input of the AND gate 538. The other input of the AND gate 538 receives the signal S(52). Thus, the production of the output signal of the AND gate 538 is inhibited during the occurrence of the signal S(536), so that the signal S(532) is produced as illustrated in FIG. 6. The width $\Delta t_2$ in the pulse S(536) corresponds to the length $\Delta x_2$ along the scanning line SC1. The widths $\Delta t_3$ and $\Delta t_4$ in the pulse S(536) correspond to the lengths $\Delta x_3$ and $\Delta x_4$ along the scanning line SC5.

As described above, the modified reference pattern 11 (MOD) is obtained from the reference pattern 11 (REF). The signal representing the thus obtained modified pattern 11 (MOD) is supplied from the pattern signal modification circuit 53 to the other input of the comparator circuit 61 and to the reference pattern display device 54.

Accordingly, the comparison between the actual pattern and the modified reference pattern is carried out in the comparator circuit 61. The comparator circuit 61 produces the output signal indicating the occurrence of inconsistency when the difference between the signal of the actual pattern and the signal of the modified reference pattern exceeds a predetermined threshold value.

Also, a visual comparison can be made by viewing patterns displayed on the actual pattern display device 42 and the reference pattern display device 54. Thus, unnecessary detection of the difference in the corners between the actual pattern 11 on the reticle 1 and the reference pattern stored in the memory device 51 is avoided.

In the device of FIG. 2, the output signal of the comparator circuit 61 is stored in the memory device 62 comprising, for example, a magnetic tape. When the comparison of one pattern is completed, the set-reset circuit 534 and the counter 63 are reset by the reset signal RESET (FIG. 3).

Figure 7:
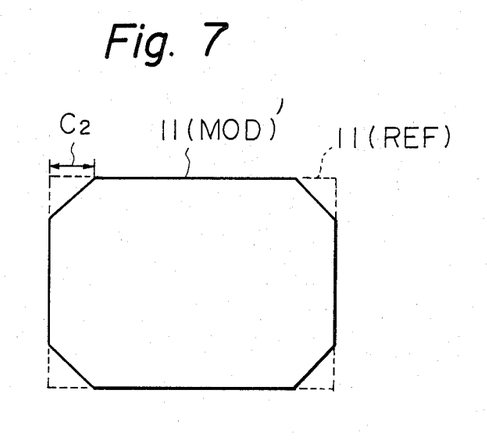
FIGS. 7 and 8 are other examples of the modified reference pattern.
Figure 8:
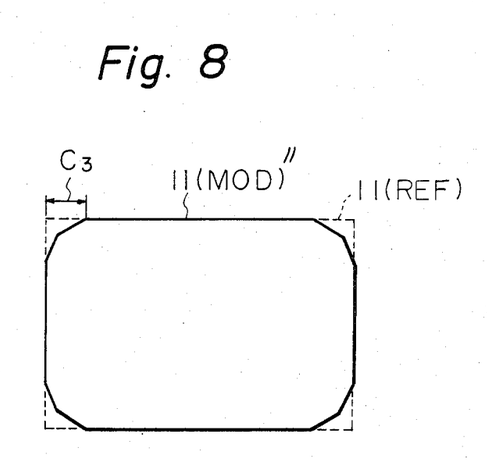

Although the preferred embodiment has been described heretofore with reference to FIGS. 2 through 6, it will be understood that various modifications or alterations are possible without departing from the scope of the present invention. For example, instead of the modified reference pattern of FIG. 5, other modified reference patterns of FIG. 7 and FIG. 8 can be used. The modified reference pattern 11 (MOD)' of FIG. 7 has corners formed by a single straight line cut. The modified reference pattern 11 (MOD)" of FIG. 8 has corners formed by a bent straight line cut. The lengths $C_2$ and $C_3$ of the corner cut portions of FIGS. 7 and 8 are, for example, approximately 0.5 micron through 2.5 micron.

We claim:

1. A method for inspecting a pattern which is produced by using pattern data for a predetermined reference pattern having corners and being stored in a memory device, comprising the steps of:

(a) scanning the pattern to be inspected to produce a scanning signal;

(b) reading out the pattern data of the predetermined reference pattern stored in the memory device;

(c) processing the pattern data of the predetermined reference pattern to provide a modified form signal corresponding to a permissible pattern which is formed by deleting corners from the predetermined reference pattern; and (d) comparing the scanning signal of the pattern and the modified form signal of the predetermined reference pattern.

2. A method as defined in claim 1, wherein said scanning step (a) comprises scanning a reticle pattern used for producing master masks for semiconductor devices.

3. An apparatus for inspecting a pattern which is produced by using pattern data of a predetermined reference pattern having corners, comprising:

scanning means for scanning the pattern to be inspected, said scanning means including:
a light source generating a light beam;
an image sensor operatively connected to sense said light beam and generate signals;
a stage for supporting the pattern; and
driving means, operatively connected to said stage, for driving said stage;

pattern signal conversion means, operatively connected to said image sensor, for receiving the signals from said image sensor and generating a scanning signal;

memory means, operatively connected to said pattern signal conversion means, for storing the pattern data of the predetermined reference pattern and providing a signal;

reference pattern signal conversion means, operatively connected to said memory means, for receiving said signal from said memory means and generating a pattern signal of the predetermined reference pattern;

signal modifying means, operatively connected to said reference pattern signal conversion means, for modifying the pattern signal of the predetermined reference pattern and generating a modified signal of the predetermined reference pattern, the modified signal corresponding to a permissible pattern which is formed by deleting the corners from the predetermined reference pattern; and comparator means, operatively connected to said pattern signal conversion means and said signal modifying means, for comparing the scanning signal from said pattern signal conversion means and the modified signal of the predetermined reference pattern from said signal modifying means.

4. An apparatus, operatively connected to a memory for storing predetermined reference pattern data, the pattern being produced from pattern data of a predetermined reference pattern, the predetermined reference pattern having corners, for inspecting a pattern supported by a stage, comprising:

scanning means for scanning the pattern and outputting a scanning signal corresponding to the pattern;

a pattern signal conversion circuit, operatively connected to said scanning means, for receiving the scanning signal and generating a pattern signal;

a reference pattern signal conversion circuit, operatively connected to the memory, for receiving the predetermined reference pattern data and outputting a converted signal; a pattern signal modifying circuit, operatively connected to the reference pattern signal conversion circuit, for modifying the pattern signal of the predetermined reference pattern and generating a modified pattern signal, accordingly, the modified pattern signal corresponding to a permissible pattern which is formed by deleting the corners from the predetermined reference pattern;

a comparator, operatively connected to said pattern signal modifying circuit and said pattern signal conversion circuit, for receiving the modified pattern signal and the pattern signal and outputting a signal corresponding to the difference between the modified pattern signal and the pattern signal; and first and second pattern display devices, operatively connected to said reference pattern signal conversion circuit and said pattern signal modifying circuit, for receiving and displaying the modified pattern signal and the pattern signal, respectively.

5. An apparatus as defined in claim 4, wherein said pattern signal modifying circuit comprises:

a change point detecting circuit, operatively connected to the reference pattern signal conversion circuit, for receiving the converted signal, detecting the edge of the pattern and outputting a first signal;

a set/reset circuit, operatively connected to said change point detecting circuit, for receiving the first signal and outputting a second signal;

a counter, operatively connected to said set/reset circuit, for receiving the second signal and outputting a third signal;

a modifying pulse generating circuit, operatively connected to said counter, for generating a modified pulse signal in accordance with the third signal;

an inverter, operatively connected to said modifying pulse generating circuit, for receiving the modified pulse signal and outputting an inverted modified pulse signal; and an AND gate, operatively connected to said inverter and said reference pattern signal conversion circuit, for receiving the inverted modified pulse signal and the converted signal and producing the modified reference pattern signal in dependence upon the modified pulse signal.

6. An apparatus as defined in claim 4, wherein said modified pattern signal is generated when the corners of the predetermined reference pattern are cut by a single straight line.

7. An apparatus as defined in claim 4, wherein said modified pattern signal is generated when the corners of the predetermined reference pattern are cut by two straight lines at an angle to each other.

8. An apparatus as defined in claim 4, wherein said modified pattern signal is generated when the corners of the predetermined reference pattern are substantially rounded.

9. A method for inspecting a pattern produced by using pattern data corresponding to a predetermined reference pattern having corners and stored in a memory device, comprising the steps of:

(a) scanning the pattern to be inspected to produce a scanning signal;

(b) reading out pattern data corresponding to the predetermined reference pattern stored in the memory device;

(c) modifying the pattern data of the predetermined reference pattern to provide a modified form signal corresponding to a permissible pattern, by the substeps of:
  (i) applying the pattern signal to a change point detecting circuit for detecting the edge of the pattern and outputting a first signal;
  (ii) supplying the first output signal to a counter which outputs a second signal;
  (iii) producing a modified form signal in accordance with the second output signal of the counter;

(d) comparing the scanning signal and the modified form signal to determine whether the pattern inspected is a correct pattern.

10. A method as defined as claim 9, wherein said step (iii) comprises producing a modified form signal corresponding to when the corners of the pattern are cut by a single straight line.

11. A method as defined in claim 9, wherein said substep (iii) comprises producing a modified form signal corresponding to when the corners of the pattern are cut by two straight lines at an angle to each other.

12. A method as defined in claim 9, wherein said substep (iii) comprises producing a modified form signal corresponding to when the corners of the pattern are substantially rounded.

* * * * *